(12) United States Patent
Han et al.

(10) Patent No.: US 7,604,982 B2
(45) Date of Patent: Oct. 20, 2009

(54) HIGH-THROUGHPUT SCREENING METHOD FOR INTERGRIN ANTAGONIST AND NEW PEPTIDE SCREENED THEREFROM

(75) Inventors: Moon-Hi Han, Daejeon (KR); In-Cheol Kang, Suwon-si (KR); Yoon-Suk Lee, Chuncheon-si (KR); Soo-Ik Chang, Cheongju-si (KR)

(73) Assignee: Proteogen Inc., Seoul (KR)

( * ) Notice: Subject to any disclaimer, the term of this patent is extended or adjusted under 35 U.S.C. 154(b) by 0 days.

(21) Appl. No.: 10/566,532

(22) PCT Filed: Nov. 26, 2004

(86) PCT No.: PCT/KR2004/003086

§ 371 (c)(1),
(2), (4) Date: Mar. 12, 2007

(87) PCT Pub. No.: WO2005/052590

PCT Pub. Date: Jun. 9, 2005

(65) Prior Publication Data

US 2007/0249061 A1    Oct. 25, 2007

(30) Foreign Application Priority Data

Nov. 29, 2003  (KR) ...................... 10-2003-0086014

(51) Int. Cl.
*C12M 3/00* (2006.01)
(52) U.S. Cl. .................................... 435/287.2
(58) Field of Classification Search ............... 435/287.2, 435/287.1, 4, 7.1, 7.92, 7.93
See application file for complete search history.

(56) References Cited

U.S. PATENT DOCUMENTS

| | | | |
|---|---|---|---|
| 6,218,136 B1 * | 4/2001 | Kumar et al. .................. | 435/15 |
| 6,617,114 B1 | 9/2003 | Fowlkes et al. | |
| 6,801,677 B1 * | 10/2004 | Grace et al. ..................... | 385/12 |
| 6,986,992 B2 * | 1/2006 | Chui et al. ....................... | 435/6 |
| 7,105,508 B1 * | 9/2006 | Kling et al. ............. | 514/212.04 |
| 2002/0102617 A1 | 8/2002 | MacBeath et al. | |

FOREIGN PATENT DOCUMENTS

JP    2004-512497    4/2004

OTHER PUBLICATIONS

International Search Report; Date of Completion Mar. 22, 2005; pp. 3; International Application No. PCT/KR2004/003086.

Dubree, Nathan J.P. et al., "Selective α4β7 Integrin Antagonists and Their Potential as Antiflammatory Agents", *J. Med. Chem.*, vol. 45:3451-3457 (Aug. 2002).
Hessel, Birgit et al., "Primary Structure of Human Fibrinogen and Fibrin, Structural Studies on $NH_2$-terminal Part of BβChain", *Eur. J. Biochem.* 98, 521-534 (1979).
Koivunen, Erkki et al., "Inhibition of $β_2$ Integrin-mediated Leukocyte Cell Adhesion by Leucine-Leucine-Glycine Motif-containing Peptides", *The Journal of Cell Biology*, vol. 153:905-916 (May 28, 2001).
Kornblihtt, Alberto R. et al., "Human Fibronectin: Cell Specific Alternative mRNA splicing Generates Polypeptide Chains Differing in the Number of Internal Repeats", *Nucleic Acids Research*, vol. 12(14): 5853-68; (Jul. 25, 1984).
Lee, Yoonsuk et al., "ProteoChip: A Highly Sensitive Protein Microarray Prepared by a Novel Method of Protein Immobilization for Application of Protein-protein Interaction Studies", *Proteomics* 3:2289-2304 (2003).
Soininen, Raija, et al., "Complete Primary Structure of the $α_1$-Chain of Human Basement Membrane (type IV) collagen", *FEBS Letters*, vol. 225 (1,2):188-194 1987).
Suzuki, Shintaro et al., "Complete Amino Acid Sequence of Human Vitronectin Deduced from cDNA. Similarity of Cell Attachment Sites in Vitronectin and Fibronectin", *The EMBO Journal*, vol. 4(10):2519-2524, (1985).
Tarui, Takehiko et al., "Plasmin-induced Migration of Endothelial Cells, A Potential Target for the Anti-Angiogenic Action of Angiostatin", *The Journal of Biological Chemistry*, vol. 277(37):33564-33570 (2002).
Titani, Koiti et al., "Amino Acid Sequence of Human von Willebrand Factor", *Biochemistry*, vol. 25: 3171-3184 (1986).
Lee et al., "Proteochip: A Highly Sensitive Protein Microarray Prepared by a Novel Method of Protein Immobilization for Application of Protein-Protein Interaction Studies", Proteomics, vol. 3, 2003. pp. 2289-2304.
Notice of Preliminary Rejection for related Japanese patent application No. 2006-535278.

* cited by examiner

*Primary Examiner*—Ann Y Lam
(74) *Attorney, Agent, or Firm*—Gerald T. Shekleton; Husch Blackwell Sanders Welsh & Katz

(57) ABSTRACT

The present invention relates to the screening method of antagonistic material of integrin using the protein chip and useful peptides screened thereby. The protein chip used in the present invention is unique substrate coated with new material, calixarene derivative, which can keep uniform and high activities of proteins. Integrin receptor protein is arrayed high densely on the chip, and materials (protein, peptide, small molecules and so on) specifically inhibiting the binding of ligand can be screened therewith. The integrins used in the present invention are integrin av f3 3 and integrin a1, b j3 3, and new antagonistic peptides screened from peptide library have high binding affinity.

3 Claims, 10 Drawing Sheets

Integrin $\alpha_{2b}\beta_3$-Fibrinogen System

| Fibrnogen | Reopro | Echistain | Flavoridin | Kistrin | Salmosin | RGD | RGE |
|---|---|---|---|---|---|---|---|
| (100ng/ml) | ($\alpha_{2b}\beta_3$ mAb) | (250µg/ml) | (250 µg/ml) | (250µg/ml) | (357µg/ml) | (250µg/ml) | (250µg/ml) |

Integrin $\alpha_v\beta_3$-Vitronectin System

Integrin $\alpha_v\beta_3$-Vitronectin system

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial sequence
<220> FEATURE:
<223> OTHER INFORMATION: integrin antagonistic peptide

<400> SEQUENCE: 1

His Ser Asp Val His Lys
1               5

<210> SEQ ID NO 2
<211> LENGTH: 6
<212> TYPE: PRT
<213> ORGANISM: Artificial sequence
<220> FEATURE:
<223> OTHER INFORMATION: integrin antagonistic peptide

<400> SEQUENCE: 2

His Gly Asp Val His Lys
1               5

<210> SEQ ID NO 3
<211> LENGTH: 6
<212> TYPE: PRT
<213> ORGANISM: Artificial sequence
<220> FEATURE:
<223> OTHER INFORMATION: integrin antagonistic peptide

<400> SEQUENCE: 3

His His Leu Leu His Lys
1               5

<210> SEQ ID NO 4
<211> LENGTH: 6
<212> TYPE: PRT
<213> ORGANISM: Artificial sequence
<220> FEATURE:
<223> OTHER INFORMATION: integrin antagonistic peptide

<400> SEQUENCE: 4

His Gly Leu Val His Lys
1               5

<210> SEQ ID NO 5
<211> LENGTH: 6
<212> TYPE: PRT
<213> ORGANISM: Artificial sequence
<220> FEATURE:
<223> OTHER INFORMATION: integrin antagonistic peptide

<400> SEQUENCE: 5

His Gly Asp Leu His Lys
1               5
```

HIGH-THROUGHPUT SCREENING METHOD FOR INTERGRIN ANTAGONIST AND NEW PEPTIDE SCREENED THEREFROM

TECHNICAL FIELD

The present invention relates to the screening method of new drug candidates using protein interaction happening after binding a small amount of protein on high sensitive protein chip and useful peptide screened thereby.

BACKGROUND ART

Functional proteomics is one of important areas of post-genome researches and this functional proteomics is expected in the future to be broadly used as a key technology for developing a new drug in several fields including protein expression pattern analysis, biomarker analysis for diagnosing disease, search of new biomarker and new drug target, and screening of candidate drugs. However, breakthrough technology for the facilitation of proteomics research is needed, and this technology is thought to be highly sensitive protein microarray chip technology. Protein chip technology is for a large amount of and concurrent analysis using reaction of chip surface on which biomolecules such as protein, antibody, peptide, ligand and so on are micro-arrayed densely, and is being rapidly developed with DNA chip according to an introduction of the importance of protein interaction and functional analysis caused by human genome map project.

Integrin receptor is cell surface receptor controlling important physiological activities of cell such as cell adhesion and migration, differentiation, proliferation and so on. Integrin works as heterodimer made by the non-covalent binding of alpha and beta subunit, and alpha and beta subunit, as pairs, constitute 22 kind of integrin family. That is, this ligand specificity is different from each kind of integrin and one kind of integrin can be bound with several ligands at the same time. The kind of ligand is really various and mainly extracellular matrix proteins (vitronectin, fibronectin, collagen, laminin, vWF, fibrinogen and so on). Integrin consists of long extracellular domain and short cytoplasmic domain, and the extracellular domain has the motif binding with ligand. Cytoplasmic domain is connected with cytoskeleton in cytoplasm, and the activation of integrin causes cytoskeleton rearrangement and forms focal adhesion complex, with which cell adhesion and migration process are performed. An antagonistic material of integrin $\alpha_v\beta_3$, for example, is one of disintegrin family derived from snake venom. About 30 materials are known as disintegrin and have a same integral-binding motif, Arg-Gly-Asp (RGD) sequence, and have an ability inhibiting the binding of integrin and ligand. These block $\alpha_{11b}\beta_3$ integrin, one of integrins present on a platelet surface and inhibit the binding of ligand fibrinogen, which suppresses platelet aggregation. Because of this characteristics of disintegrin, the disintegrin works as an antagonistic material of integrin $\alpha_v\beta_3$ and thus suppresses angiogenesis.

Phase 1 clinical trial of Vitaxin, a humanized mAb against integrin $\alpha_v\beta_3$, for treating solid tumor has been successfully established without any severe toxicity and Phase 2 clinical trial is being performed now. An interesting fact is that the cancer tissue of one patient among 12 patients of clinical trial decreased by over 50%. EMD121974 developed by Merck company is a small molecule (cyclic RGD peptide) inhibiting endothelial integrin $\alpha_v\beta_3$, and its phase 1 clinical trial is being done. This material is a cyclic pentapeptide having RGD sequence and is shown through animal test to have an activity inhibiting angiogenesis and thus suppressing cancer growth in human malignant melanoma and so on. Mechanism of endostatin has not been understood for a long time, but recently recombinant human endostatin is established to interact with blood endothelial alpha(5) and alpha(v)-integrin and thus inhibit integrin-dependent endothelial function such as endothelial cell migration. Therefore, these results demonstrate that it is possible to develop an antagonistic material of integrin as angiogenesis inhibitor for treating cancer.

Technology used until now for searching antagonistic material of integrin is Enzyme Linked Immuno Sorbent Assay (ELISA), one of technologies broadly used for diagnosis in research center or hospital. However, this method is not appropriate for large screening because it needs a large amount of protein and is non-specific.

DISCLOSURE OF INVENTION

The present invention provides a high-throughput screening method of inhibitory material reacting to integrin, using a protein chip. The present invention also provides new useful peptide screened by the above screening method of inhibitory material of integrin.

More in detail, to achieve the above purpose, the present invention provides a high-throughput screening method of antagonistic material of integrin, comprising the steps of: immobilizing integrin $\alpha_{11b}\beta_3$ and/or $\alpha_v\beta_3$ on a protein chip; reacting ligand protein labeled with fluorescence and peptide pool of peptide library on the protein chip on which the integrin is immobilized; washing the protein chip with buffer solution after the reacting; and measuring the degree of ligand binding after the washing.

In a preferable embodiment of the present invention, the above ligand is any one selected from the group consisting of vitronectin (EMBO J. 1985 October; 4(10): 2519-24), fibronectin (Nucleic Acids Res. 1984 Jul. 25; 12(14): 5853-68), collagen (FEBS Lett. 1987 Dec. 10; 225(1-2): 188-94), laminin (Lab Invest. 1989 June; 60(6): 772-82), Von Willebrand Factor (vWF; Biochemistry. 1986 Jun. 3; 25(11): 3171-84) and fibrinogen (Thromb Haemost. 1979 Jun. 30; 41(4): 662-70).

The present invention also provides useful peptides, such as HSDVHK peptide (SEQ ID NO: 1), HGDVHK peptide (SEQ ID NO: 2), HHLLHK peptide (SEQ ID NO: 3), HGLVHK peptide (SEQ ID NO: 4) and HGDLHK peptide (SEQ ID NO: 5), having antagonistic activity of integrin and screened by the above screening method.

BRIEF DESCRIPTION OF THE DRAWINGS

These and other features, aspects, and advantages of preferred embodiments of the present invention will be more fully described in the following detailed description, taken accompanying drawings. In the drawings.

BEST MODES FOR CARRYING OUT THE INVENTION

Figure 1:
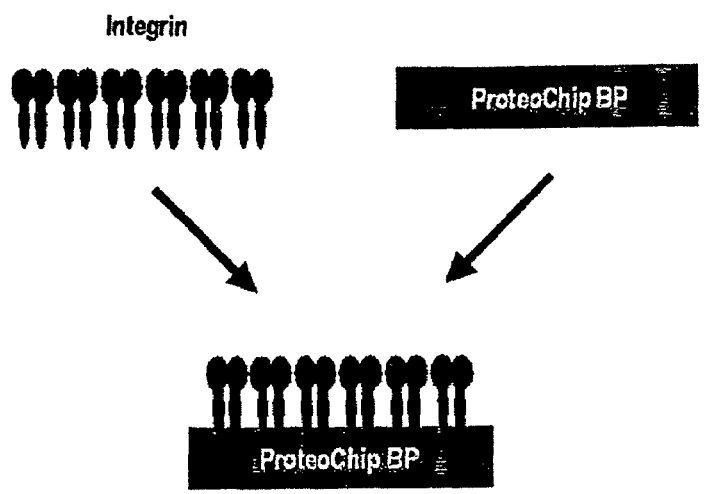
FIG. 1 is a schematic diagram showing an immobilization method of integrin receptor on the protein chip, ProteoChip™.

In a embodiment of the present invention, ProteoChip™ (Proteogen, Inc., Seoul, South Korea) can be used as protein chip. ProteoChip™ is a aminated glass slide coated with calixarene derivative and calixarene derivative works as bifunctional molecular linker (See Han M. H. et al.: Proteo-Chip, its fabrication method and detection of protein using ProteoChip, Korea patent application No. 2002-41770, 2002 and Lee, Y. S. et al.: ProteoChip: a highly sensitive protein microarray proposed by a novel method of protein immobilization for application of protein-protein interaction studies, *Proteomics* 2003; 3: 2289-2304). After immobilizing integrin receptor on ProteoChip™ (purchased from Proteogen Inc.) to make an integrin monolayer, it was evaluated whether high-throughput screening of the most suitable peptide inhibiting ligand binding was possible or not by mixing ligand protein labeled with fluorescence and peptides having randomized sequences.

Firstly, the experiment of evaluating the binding affinity of integrin-ligand was performed to investigate the stability of integrin receptor immobilized on the chip, which result revealed that ligand was bound with integrin immobilized on the chip in a dose-dependent manner, which confirms there is no problem in the stability of the immobilized integrin receptor. Whether integrin-ligand interaction is inhibited or not is also investigated using known antagonistic materials of integrin such as disintegrin and monoclonal antibody against integrin. The result demonstrated that all these proteins effectively and competitively inhibited integrin-ligand interaction on ProteoChip™. Actually, a large screening test was performed on ProteoChip™ using integrin-ligand interaction inhibition assay with peptide library having peptides having about 2 millions randomized and different sequences, and a peptide having the most suitable amino acid sequence was searched thereby. These results prove that ProteoChip™ can be used for screening new materials inhibiting integrin-ligand interaction and can be used as a screening method of new drug development.

Hereinafter, non-limiting and preferred embodiments of the present invention will be described in detail with reference to the accompanying drawings.

EXAMPLE 1

Immobilization of Integrin Receptor on Protein Chip

ProteoChip™ (Proteogen, Inc., Seoul, South Korea) was used as a protein chip and integrins were spotted on the ProteoChip™ (Proteogen, Inc., Seoul, South Korea) with the microarrayer (CM-1000; Proteogen, Inc., Seoul, South Korea) to fabricate integrin receptor microarray (See Lee, Y. S. et al.: ProteoChip: a highly sensitive protein microarray proposed by a novel method of protein immobilization for application of protein-protein interaction studies, *Proteomics* 2003; 3: 2289-2304). Integrin $\alpha_{11b}\beta_3$ was purified to homogeneity by GRGDSPK-Sepharose column chromatography from the platelet (See Kang I. C. and Kim D. S., Analysis of potent glycoprotein IIb-IIIa antagonist from natural sources. *J Biochem Mol Biol* 1998; 31: 515-518), and Integrin $\alpha_\nu\beta_3$ was commercially obtained from Chemicon International, Inc. (CA, USA).

Integrins (40 µg/mL) diluted with a phosphate-buffered saline (PBS) solution containing 10 mM β-octylthioglucopy-ranoside, 1.0 mM $CaCl_2$, 11.0 mM $MgCl_2$, and 30% glycerol were spotted and incubated at 37° C. for 3 hours, and then the remaining integrins after binding were washed with 0.5% PBST (PBS containing 0.5% Tween-20). The prepared integrin microarray was stored at 4° C. until before use. This integrin microarray (integrin-binding protein chip) was used for high-throughput screening of integrin receptor antagonist (See FIG. 1).

EXAMPLE 2

Integrin-Ligand Interaction Assay Using Integrin Microarray

The ligand proteins (fibrinogen or vitronectin; Chemicon International, Inc., USA) labeled with fluorescence (Cy-5 or Cy-3; Amersham-Pharmacia Biotech, USA) were spotted with the microarrayer on the integrin-binding protein chip prepared in Example 1 in different concentrations ranging from 1 µg/ml to µg/ml, and then incubated in a oven of 37° C. and over 75% humidity for 1 hour. After washing by immersing in 0.5% PBST for 10 minutes, results of integrin-ligand interaction were measured by a fluorescence scanner.

Figure 2:
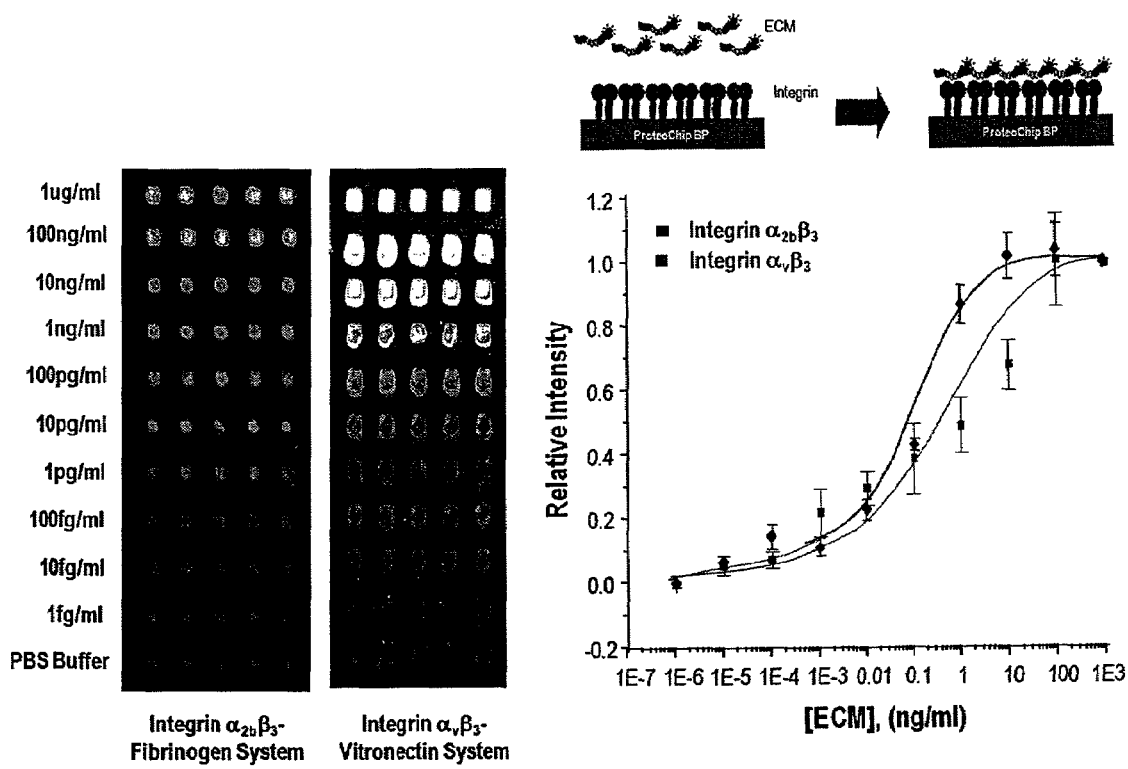
FIG. 2 is a schematic diagram showing the experimental result of integrin-ligand interaction using the protein chip, ProteoChip™.

Relative intensities of fluorescence according to the concentrations were shown as linear in graph, from which the detection limit is shown to be at a concentration of 1 fg/ml (See FIG. 2).

EXAMPLE 3

Binding Inhibition Assay of Integrin $\alpha_{11b}\beta_3$-Fibrinogen Interaction by Antagonistic Materials of Integrin Mixtures of ligand protein (fibrinogen 100 ng/ml) labeled with fluorescence (Cy-5) and known integrin antagonists such as disintegrins (echistatin 250 µg/ml, flavoridin 250 µg/ml, kistrin 250 µg/ml, and salmosin 2.6 ng/ml), a monoclonal antibody (mAb) against integrin 1.0 mg/ml, and various concentrations of synthetic RGD peptides (echistatin, flavoridin, kistrin: Sigma-Aldrich, USA; Salmosin: isolated and purified from recombinant E. Coli; monoclonal antibody against integrin: Chemicon International, Inc., USA; synthetic. RGD peptides: synthesized in the Korea Research Institute of Bioscience and Biotechnology, South Korea) were dropped on the integrin receptor of integrin $\alpha_{11b}\beta_3$-binding protein chip prepared in Example 1 by using micropipette or microarrayer (CM-1000; Proteogen, Inc., Seoul, South Korea) and then were reacted in a oven of 37° C. and over 75% humidity for 4-12 hours. After reaction, those were washed for about 10 minutes with 0.5% PBST containing 3% BSA. Competitive inhibitory abilities of antagonists were measured by analyzing the degree of ligand binding as relative fluorescence intensity with a fluorescence scanner. As a result, groups treated with known integrin antagonists relatively showed a significantly low fluorescence intensity, which proves that these materials effectively inhibit integrin $\alpha_{11b}\beta_3$-fibrinogen interaction (See FIG. 3).

Figure 3:
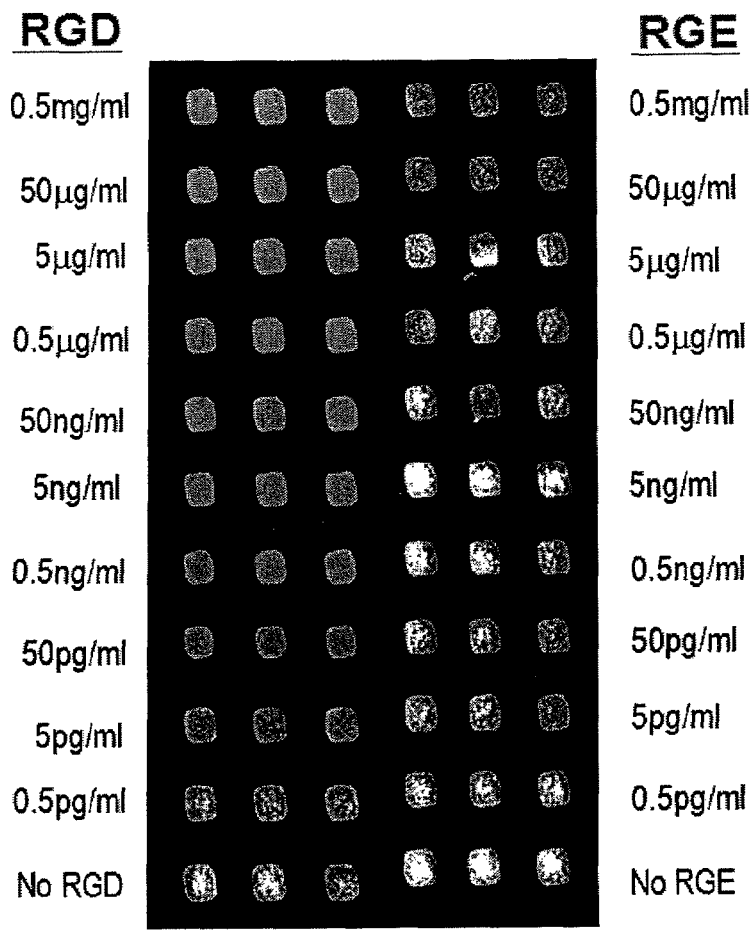
FIG. 3 shows experimental results of inhibition of integrin $\alpha_{11b}\beta_3$-fibrinogen interactions, an example of the above integrin-ligand interaction, by integrin antagonists. RGE and RGD used in experiments were synthesized with an automated peptide synthesizer and were purchased from companies, which synthesize these peptides at client's request. What was used in experiments had 6 amino acids and the amino acid sequence of RGE or RGD in the middle. Generally integrin. $\alpha_{11b}\beta_3$ binds with the amino acid sequence of RGD, which inhibits interaction of fibrinogen and integrin $\alpha_{11b}\beta_3$. However, this inhibition is not made by RGE because the RGE doesn't bind with integrin $\alpha_{11b}\beta_3$. The results are shown in FIG. 3.
Figure 3:
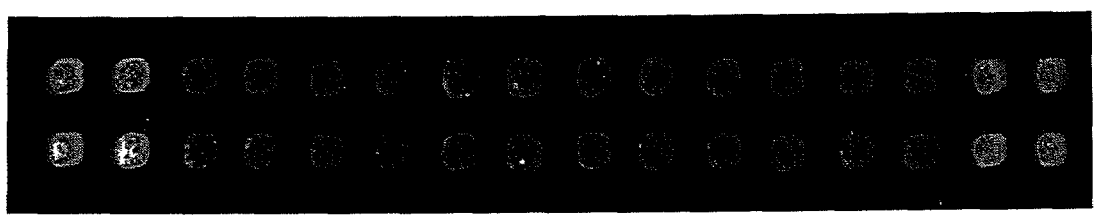

RGE and RGD used in experiments of FIG. 3 were synthesized with an automated peptide synthesizer and were purchased from companies, which synthesize these peptides at client's request. What was used in experiments had 6 amino acids and the amino acid sequence of RGE or RGD in the middle. Generally integrin $\alpha_{11b}\beta_3$ binds with the base sequence of RGD, which inhibits interaction of fibrinogen and integrin $\alpha_{11b}\beta_3$. However, this inhibition is not made by RGE because the RGE doesn't bind with integrin $\alpha_{11b}\beta_3$. The results are shown in FIG. 3. That is to say, this is a result analyzing whether mixing several concentrations of RGD or RGE with fibrinogen labeled with some concentration of fluorescence on integrin $\alpha_{11b}\beta_3$-spotted chip does inhibitory roles or not. The fluorescence intensity was measured as a result with a fluorescence scanner. The originally occurred one kind of color such as red color or blue color is difficult to be used for evaluating the fluorescence intensity, so that the instrument's software changes the color on the basis of fluorescence intensity. Thus the fluorescence intensity is expressed in color order of white, red, orange, yellow, green and blue, and the white color is usually the highest of fluorescence intensity. The group of mixing RGE (with various concentrations) and fibrinogen showed white or red color, which demonstrated that RGE can not inhibit the interaction between integrin $\alpha_{11b}\beta_3$ and fibrinogen. However, the group of mixing RGD (with various concentrations) and a concentration of fibrinogen showed the color change of from white to yellow in a concentration-dependent manner. These results demonstrated that the fluorescence intensities decrease because RGD blocks fibrinogen from binding with integrin.

EXAMPLE 4

Binding Inhibition Assay of Integrin $\alpha_v\beta_3$-Vitronectin by Antagonistic Materials of Integrin Mixtures of ligand protein (vitronectin 100 ng/ml) labeled with fluorescence (Cy-3) and known integrin antagonists such as disintegrins (echistatin 250 µg/ml, flavoridin 250 µg/ml, kistrin 250 µg/ml, and salmosin 2.6 ng/ml), a monoclonal antibody (mAb) against integrin 11.0 mg/ml, and various concentrations of synthetic RGD peptides (echistatin, flavoridin, kistrin: Sigma-Aldrich, USA; Salmosin: isolated and purified from recombinant E. Coli; monoclonal antibody against integrin: Chemicon International, Inc., USA; synthetic ROD peptides: synthesized in the Korea Research Institute of Bioscience and Biotechnology, South Korea) were dropped on the integrin receptor of the integrin $\alpha_v\beta_3$-binding protein chip prepared in Example 1 by using micropipette or microarrayer (CM-1000; Proteogen, Inc., Seoul, South Korea) and then were reacted in a oven of 37° C. and over 75% humidity for 4-12 hours. After reaction, those were washed for about 10 minutes with 0.5% PBST containing 3% BSA. Competitive inhibitory abilities of antagonists were measured by analyzing the degree of ligand binding as relative fluorescence intensity with a fluorescence scanner. As a result, groups treated with known integrin antagonists relatively showed significantly low fluorescence intensities, which proves that these materials effectively inhibit integrin $\alpha_v\beta_3$-vitronectin interaction (See FIG. 4).

Figure 4:
FIG. 4 shows experimental results of inhibition of integrin $\alpha_\nu\beta_3$-vitronectin interactions by integrin antagonists.

Antagonists used in FIG. 4 are already known as antagonistic material of integrin $\alpha_v\beta_3$-vitronectin. This is also a result analyzing whether mixing antagonists and vitronectin labeled with fluorescence inhibit or not the interaction between integrin $\alpha_v\beta_3$ and vitronectin. Control are the group having only vitronectin labeled with fluorescence without antagonists and the other groups are the results performed with antagonists and peptides including the amino acid sequence of RGE. The fluorescence intensity in FIG. 4 is expressed as rainbow colors like the explanation of FIG. 3. As shown in results, control having only vitronectin labeled with fluorescence and groups having the peptides including ROE showed white or red as the color of fluorescence, which means that integrin $\alpha_v\beta_3$ interacts with vitronectin. However, in case of groups having antagonists, antagonists inhibited the interaction between integrin $\alpha_v\beta_3$ and vitronectin, that is, integrin $\alpha_v\beta_3$ didn't bind to vitronectin, which made the color of fluorescence blue, the lowest color.

EXAMPLE 5

Figure 5:
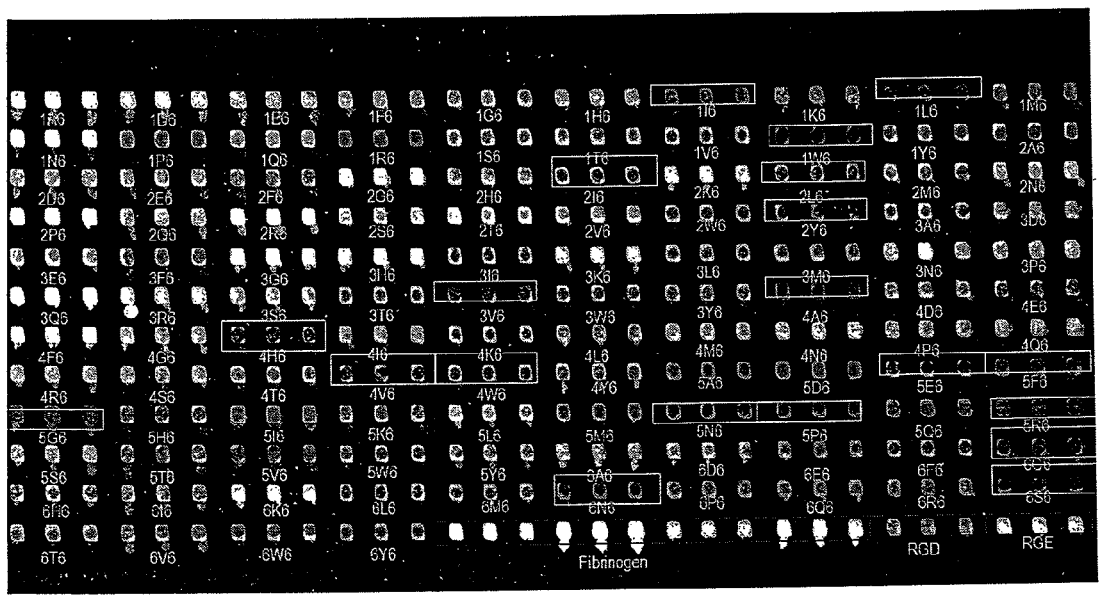
FIG. 5 shows experimental results of screening peptide antagonist of integrin $\alpha_{11b}\beta_3$. The fluorescence intensity is expressed as rainbow color. As used herein, the first number of the term "1A6" means the location where a specified amino acid is modified, the second letter of the term "1A6" Means the specified amino acid, and the last number of the term "1A6" means the length of the peptide. For example, 2H6 is a hexapeptide having a histidine at position 2.
Figure 6:
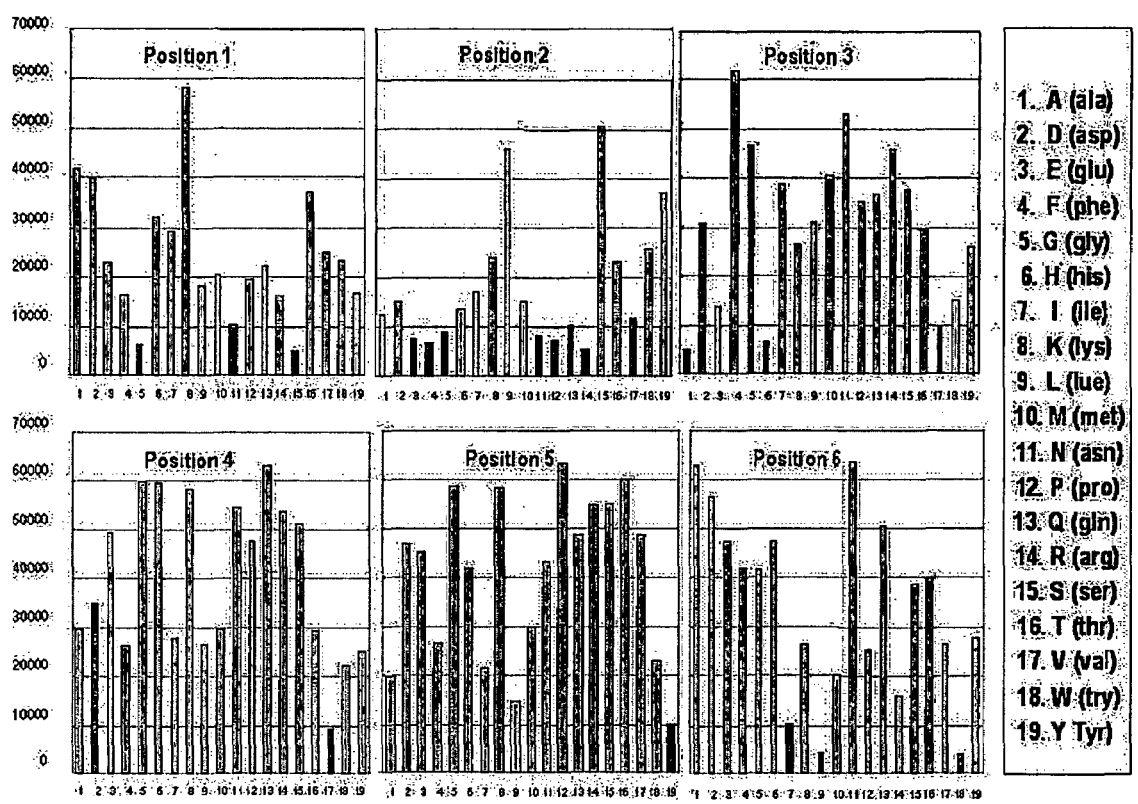
FIG. 6 is graphs drawn with the numbers calculated with the experimental results of FIG. 5, that is, the fluorescence intensities. The yellow bar of graph means that the fluorescence intensity is from about 30% to about 50% compared than the group having only fibrinogen and the red bar means that the fluorescence is less than about 20%. The numbers of from 1 to 19 marked below in each graph mean the amino acids stated in left box and position number means the location where the amino acid is fixed. For example, a bar of x-axis number 1 of position 1 graph means a hexapeptide having a alanine at position 1. Numbers of y-axis mean the fluorescence intensity and the maximum intensity is 65535. The shorter a bar is, the stronger the inhibitory activity is.
Figure 7:
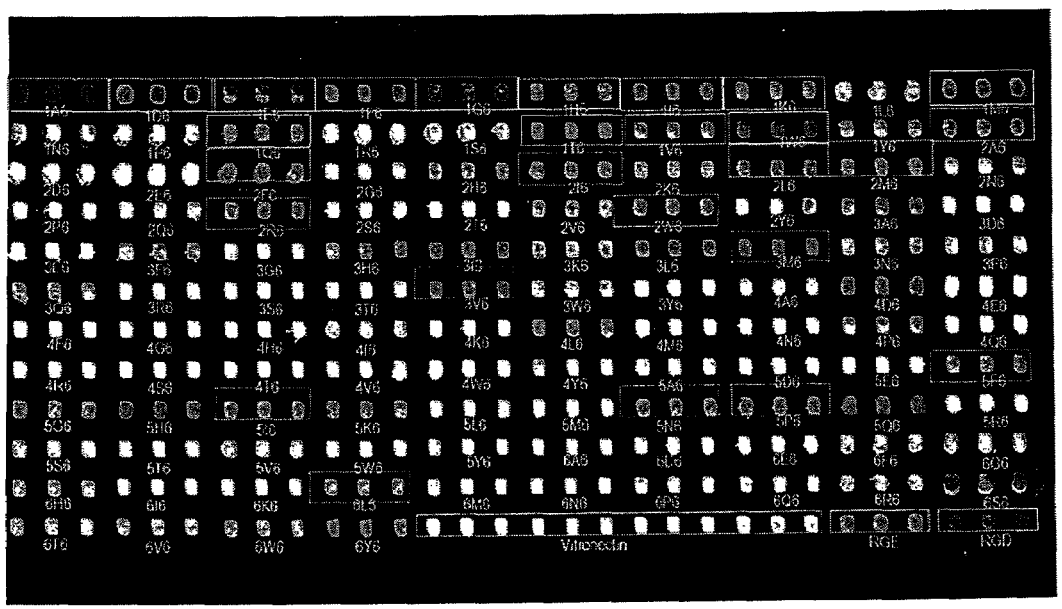
FIG. 7 is experimental results using integrin $\alpha_\nu\beta_3$ with the same method of FIG. 5.
Figure 7:
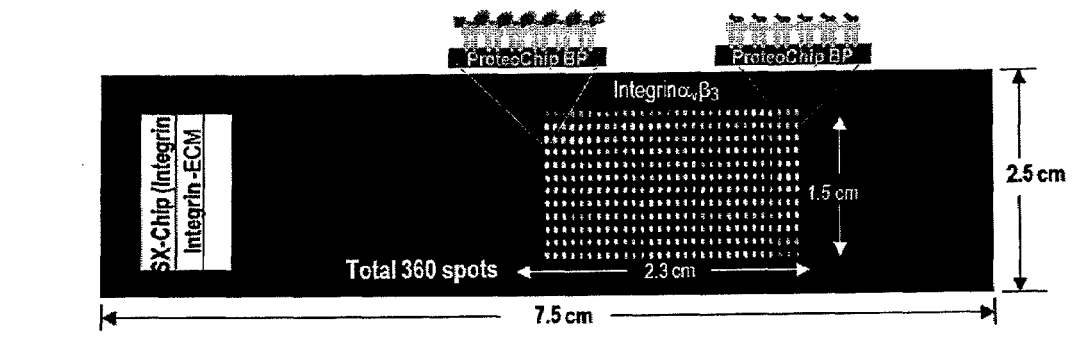
Figure 8:
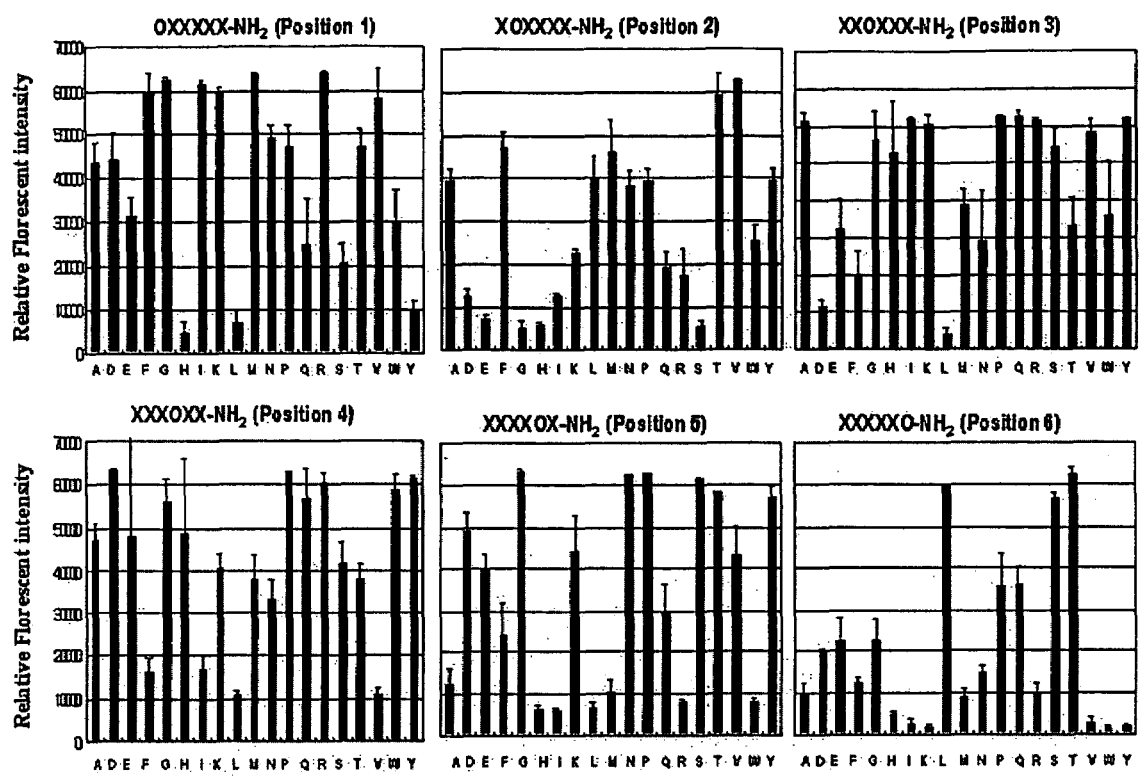
FIG. 8 is experimental results using integrin $\alpha_\nu\beta_3$ with the same method of FIG. 6.

High-Throughput Screening of Peptide Inhibitors of Integrin Receptors from Peptide Library Using the Integrin Microarray Mixtures of ligand protein (Fibrinogen 100 ng/ml and vitronectin 100 ng/ml) labeled with fluorescence (Cy-3) and 114 peptide pools from peptide library were dropped on the integrin receptor of integrin $\alpha_v\beta_3$-binding protein chip prepared in Example 1 by using micropipette or microarrayer (CM-1000; Proteogen, Inc., Seoul, South Korea) and then were reacted in oven of 37° C. and over 75% humidity for 4-12 hours. After reaction, those were washed for about 10 minutes with 0.5% PBST containing 3% BSA. Competitive inhibitory abilities of antagonists were measured by analyzing the degree of ligand binding as relative fluorescence intensity with a fluorescence scanner. As a result, there were some peptides showing relatively much lower fluorescence intensity than RGD peptides, known integrin antagonists, which thus proved that these peptides have stronger binding activity with integrin $\alpha_v\beta_3$ than synthetic RGD peptide. Peptide sequences marked with a rectangle reveal peptides having inhibitory ability (See FIGS. 5 and 7). Peptide sequences specifically binding with integrin $\alpha_v\beta_3$ and having inhibitory ability were determined on the basis of these results, and biological abilities of these were analyzed in the following FIGS. 9, 10, 11, 12 and 13. Each peptide sequence has a new amino acid sequence totally different from amino acid sequence known as integrin binding motif (for example, RGD, LDV and so on). From these results, the fact is proved that the integrin microarray of the present invention is a useful tool for screening peptide antagonist. Furthermore, these results mean that integrin microarray using ProteoChip™ can be used for screening new drug candidate.

EXAMPLE 6

Inhibitory Effect Analysis of a Screened Antagonistic Peptide According to the Amino Acid Sequence New peptides having integrin $\alpha_v\beta_3$-specific inhibitory activity were identified through the competitive inhibition assay of example 3-5 (See table 1 and 2). Table 1 shows the sequence of antagonistic peptide screened with the integrin microarray. As shown in table 1, hexapeptides having histidine or leucine at position 1 have relatively better inhibitory effect compared than the others. Hexapeptides having glutamate or glutamine at position 1 have some inhibitory effects, but the strength of these effects is lower than hexapeptides having histidine, leucine or tyrosine. Amino acids of one position of hexapeptides inhibiting integrin $\alpha_v\beta_3$-vitronectin interaction are shown in below table 1. Major inhibition means that the inhibition is 80% and more, and minor inhibition means that the inhibition is 50% and less. The results were obtained from three separate experiments.

TABLE 1

| Amino acid position in hexapeptide sequence | Amino acid of hexapeptide showing inhibitory effect on integrin chip | |
|---|---|---|
| | Major inhibition | Minor inhibition |
| 1 | H, L, Y | E, Q, S, W |
| 2 | G, S, H | L, Q, R, W |
| 3 | L, V | E, F, N |
| 4 | I, H, L, R, W | F, I |
| 5 | W, K, Y, I, V, H | F, Q |
| 6 | A, F, M, R | D, E, G, N |

12 peptides predicted to have integrin $\alpha_v\beta_3$-specific inhibitory activity were synthesized from the above results, and subjected to a test for the competitive inhibition assay against the integrin $\alpha_v\beta_3$-vitronectin interaction in a dose-dependent manner. That is, the intensity of inhibitory activity according to the amino acid sequence was investigated. Synthetic peptides inhibiting $\alpha_v\beta_3$-vitronectin interaction and their inhibition concentration are shown in the below table 2. Inhibition was quantified as the half-maximal inhibition concentration in antagonistic activity relative to the control without peptides and ND means that no activity was detected.

TABLE 2

| Number | Peptide | IC$_{50}$(pg/ml) |
|---|---|---|
| 1 | HGLLHK-NH$_2$ | ND |
| 2 | HSLLHK-NH$_2$ | ND |
| 3 | HHLLHK-NH$_2$ | 3.4 |
| 4 | HGDLHK-NH$_2$ | 30.7 |
| 5 | HSDLHK-NH$_2$ | ND |
| 6 | HHDLHK-NH$_2$ | ND |
| 7 | HGLVHK-NH$_2$ | 2.43 |
| 8 | HSLVHK-NH$_2$ | 46 |
| 9 | HHLVHK-NH$_2$ | 313 |
| 10 | HGDVHK-NH$_2$ | 44.7 |
| 11 | HSDVHK-NH$_2$ | 1.74 |
| 12 | HHDVHK-NH$_2$ | ND |

HSDVHK and HGDVHK showed the stronger inhibitory activity in integrin $\alpha_v\beta_3$-specific inhibitory test than GRGDSP, a known antagonist. However, HHDVHK didn't reveal any inhibitory activity. Amino acids of position 2, 3 and 4 (amino acids of position 2 of hexapeptide are Gly, Ser, and His; amino acids of position 3 are Leu and Asp; and amino acids of position 4 are Leu and Val) are expected to do important roles in antagonistic activity. HSDVHK is the most effective among peptides having the inhibitory activity. The results are also a proof showing that amino acid sequence-specific antagonistic activity can be accurately measured with integrin microarray using ProteoChip™. Therefore, the integrin microarray of the present invention is believed to be a tool for sensitively and accurately analyzing protein-protein interaction.

EXAMPLE 7

Figure 9:
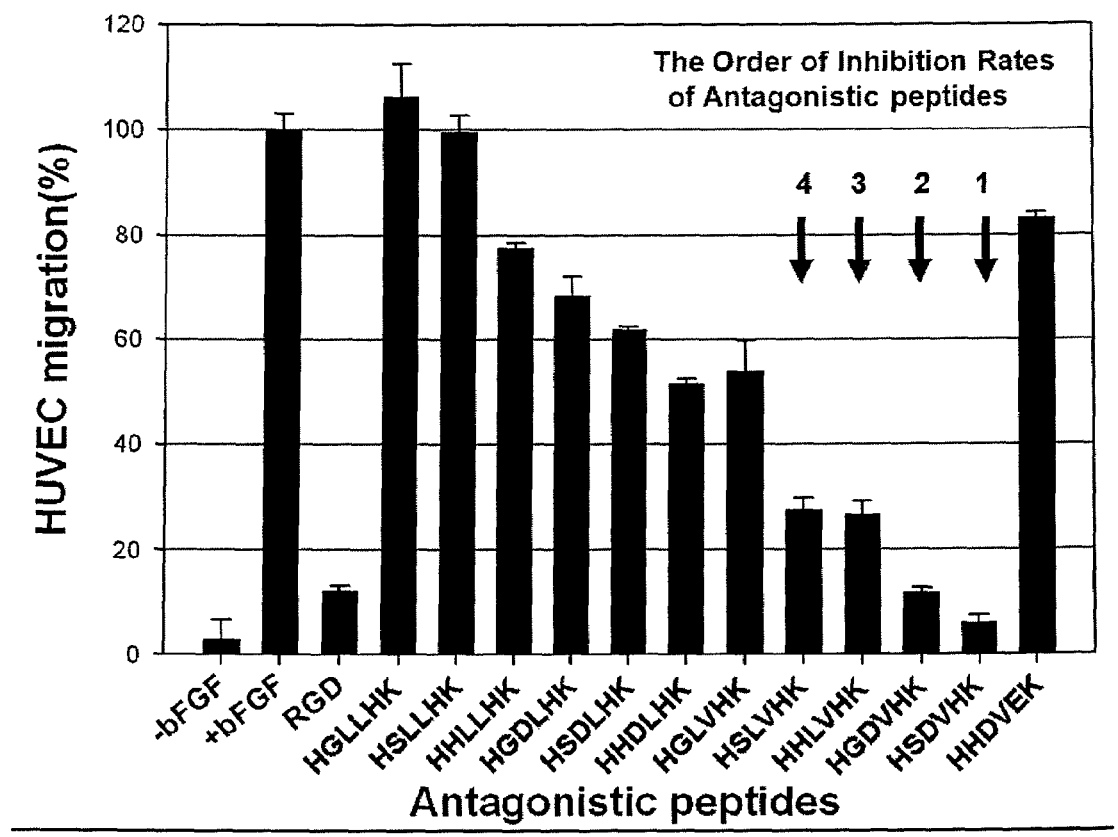
FIG. 9 is the result of analyzing effects of antagonistic peptides of integrin $\alpha_\nu\beta_3$ on migration of human umverical vein endothelial cell (HUVE cell). This is the result of in vitro endothelial cell migration test performed as one of biological characterization researches of the antagonistic peptides.
Figure 10:
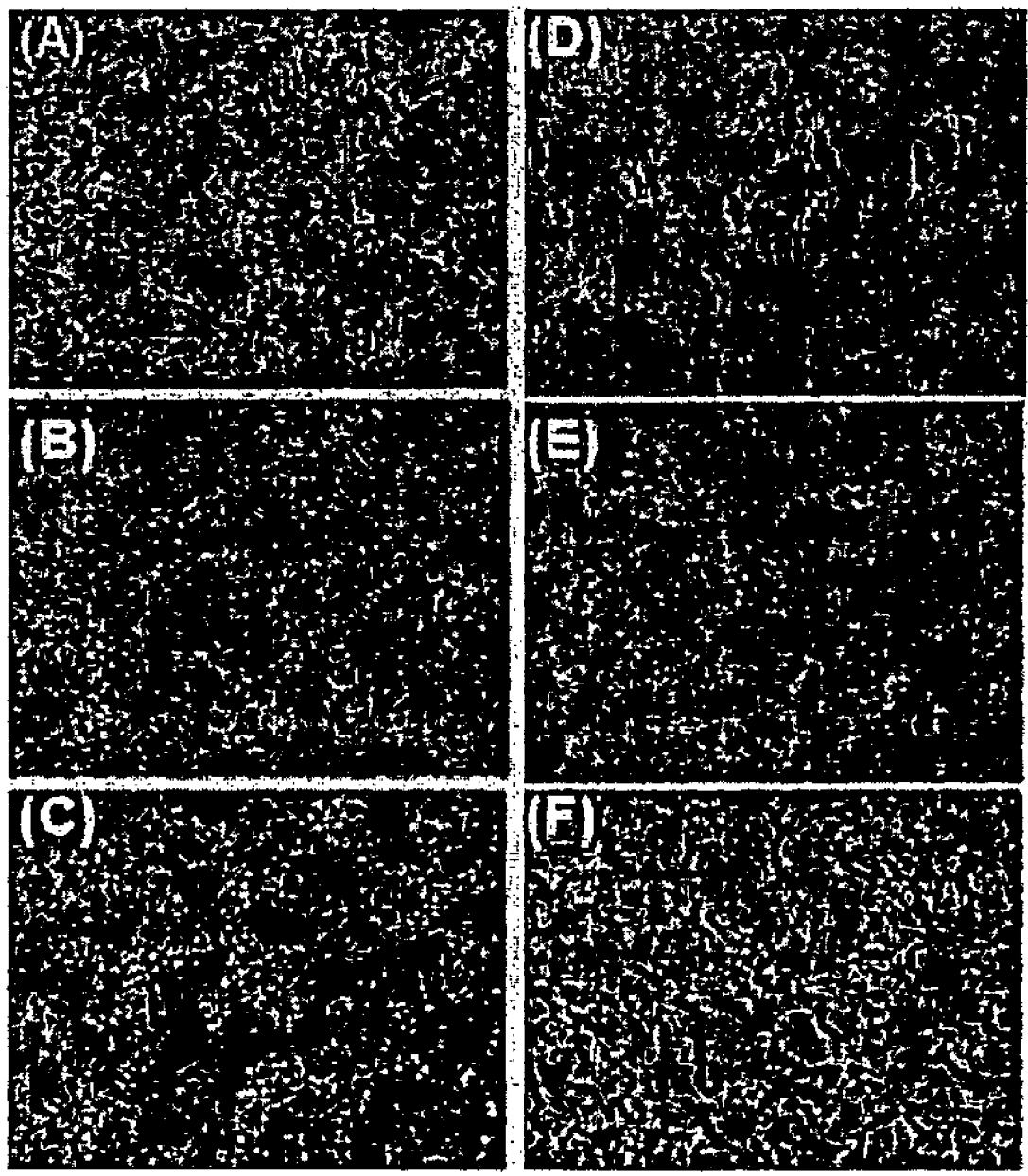
FIG. 10 is the result of analyzing effects of antagonistic peptides of integrin $\alpha_\nu\beta_3$ on angiogenesis in a chick chorio-allantoic membrane. In vivo angiogenesis inhibition test was performed as one of biological characterization researches of the antagonistic peptides. A, positive control, is the result of the group treated with only bFGF without peptide; B, negative control, is the result of the group having only cells without bFGF; C is the result of the group treated with GRGDSP peptide in the presence of bFGF; D is the result of the group treated with HGDVHK peptide in the presence of bFGF; E is the result of the group treated with HSDVHK peptide in the presence of bFGF; and F is the result of the group treated with HHDVHK peptide in the presence of bFGF.
Figure 11:
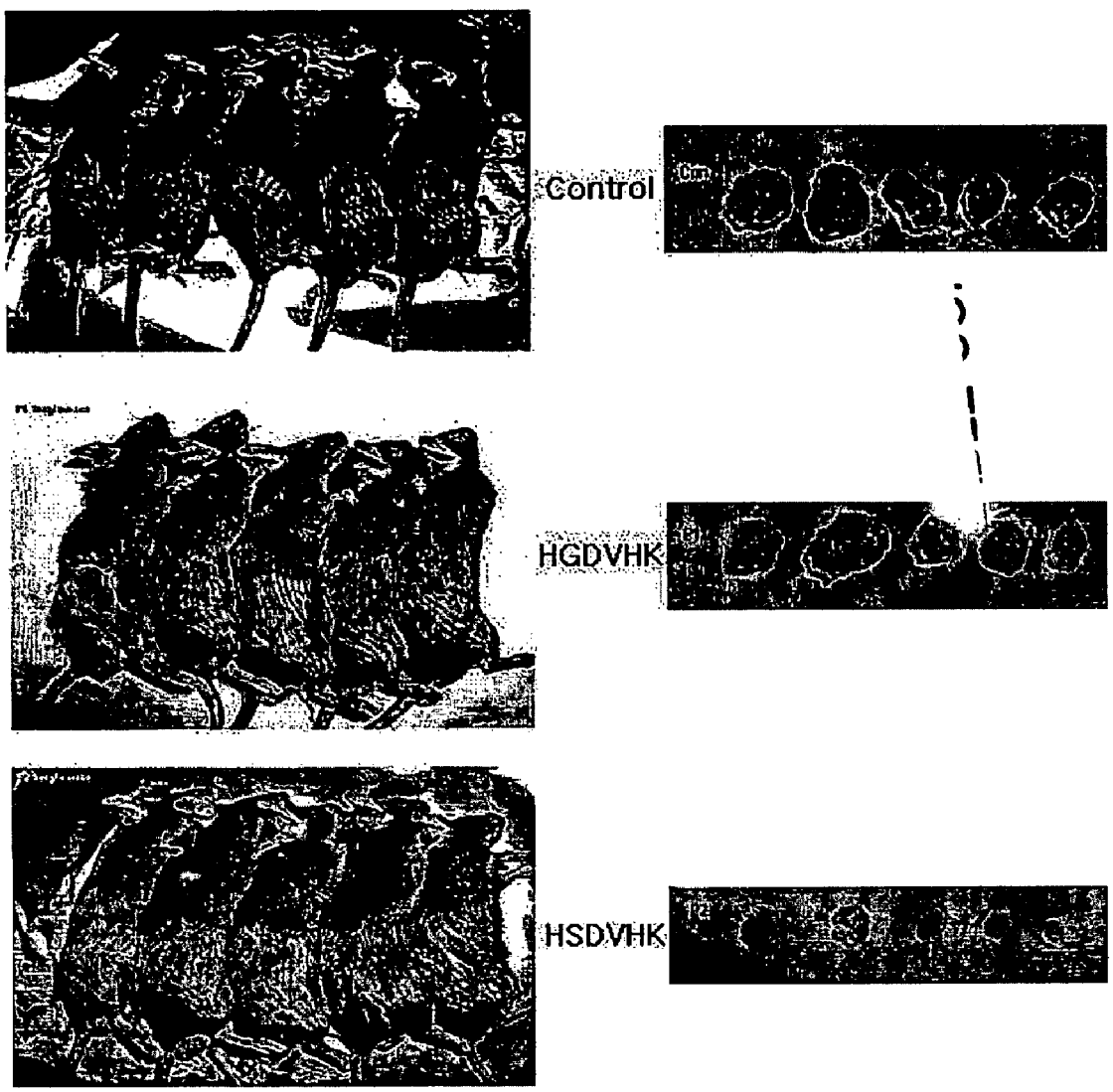
FIG. 11 is pictures of experimental results evaluating effects of antagonistic peptides of integrin $\alpha_\nu\beta_3$ in growth inhibition assay of subcutaneous solid tumor using C57BL/6 mice administered with Lewis lung carcinomas cells.
Figure 12:
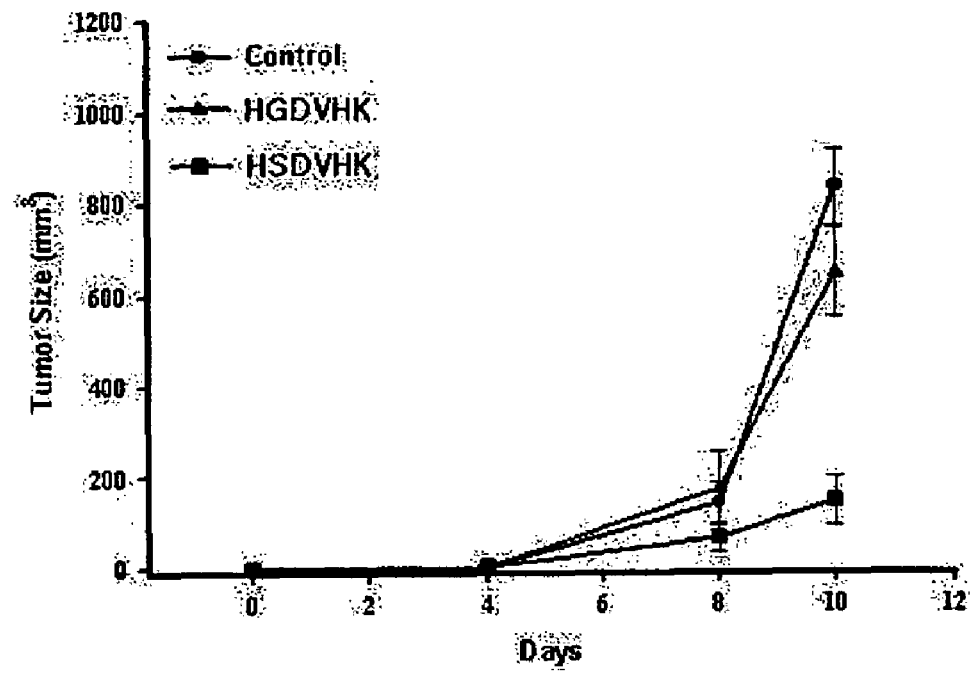
FIG. 12 is experimental results showing the changing size of tumor according to administration of antagonistic peptides of integrin $\alpha_\nu\beta_3$ in growth inhibition assay of subcutaneous solid tumor using C57BL/6 mice administered with Lewis lung carcinomas cells.
Figure 13:
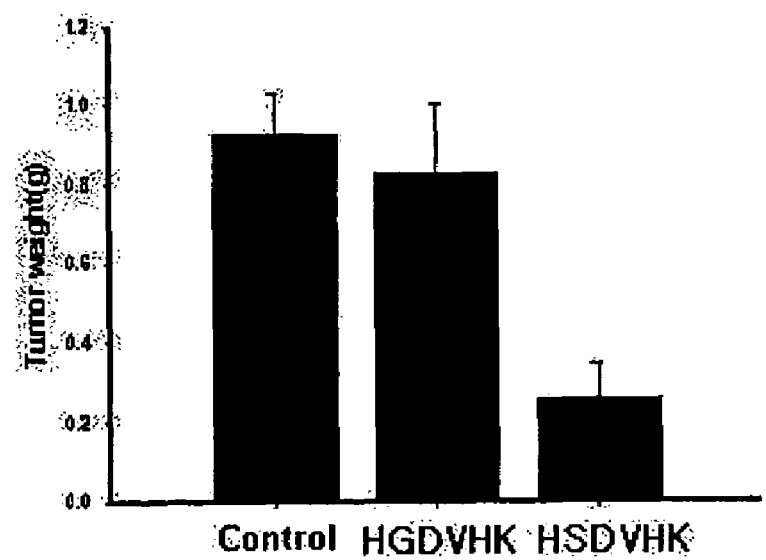
FIG. 13 is experimental results showing the changing weight of tumor according to administration of antagonistic peptides of integrin $\alpha_\nu\beta_3$ in growth inhibition assay of subcutaneous solid tumor using C57BL/6 mice administered with Lewis lung carcinomas cells.

Biological Activity Analysis of Antagonistic Peptide Screened by Using Integrin Microarray 7-1) Human Umverical Vein Endothelial Cell (HUVEC) Migration Assay HUVE cell was cultured in M199 medium containing 10% fetal calf serum and 3 ng/ml bFGF. This cell was cultured in the control medium (M199 containing 0.1% BSA) for 16 hours to be used in migration assay, and then 3×10$^4$ cells were added to upper chamber of porous membrane coated with gelatin (40 μM) and inserted in Boyden chamber. Samples were treated at the same time in a concentration-dependent manner. Chemoattractant, bFGF, was added in the bottom chamber to induce HUVE cell to migrate into lower chamber. The chamber was incubated for 4 hours at 37° C. and then the membrane was removed. After fixation, cell was stained with crystal violet and cells migrating across the membrane were counted with a microscope. The result was shown in FIG. 9. As shown in FIG. 9, HSDVHK and HGDVHK significantly inhibited human umverical vein endothelial cell (HUVEC) migration, whereas HHDVHK had little effect. From this result, biological activities of integrin $\alpha_v\beta_3$-specific inhibitory peptides are identified.

7-2) Inhibition Assay of Angiogenesis in a Chick Chorioallantoic Membrane

① Experimental Materials and Reagent Preparation

Fertilized eggs was purchased from Pulmuone Corp. (South Korea), Thermanox coverslips for sample loading was purchased from Nunc Company (USA), and 10% Intralipose (fat emulsion) for observation and syringes were purchased from Green Cross Company (South Korea).

② Experimental Step (Process)

On day 1 (0-day embryo): Fertilized egg was incubated in a incubator of 37-38° C. and over 90% humidity. The temperature and humidity were often checked to make sure the above conditions.

On day 3 (2-day embryo): The peaked end of fertilized egg was cracked with a knife. The fertilized egg was placed horizontally and then made had a pore with 5 ml syringe, and about 2 ml albumin was extracted from the pore. The pore was sealed with transparent tape to block infection and dryness of the fertilized egg. The egg was incubated again with the direction of pore toward the bottom.

On day 4 (3-day embryo): The window which diameter is 2-3 cm was made in the direction of air sac of fertilized egg (in the opposite direction of the above syringe pore) and the eggs confirmed as fertilized egg were sealed with broad transparent tape and incubated again. For reference, round window was made as follows. A round shape of scratch was made on the eggshell with a sharp knife and eggshell then was taken away with a pincette.

On day 5 (4.5-day embryo): CAM is usually created at this time and the diameter is about 2-5 mm. Sample was dissolved in suitable solvent (ddH$_2$O, ethanol and so on) and then 10 μl sample was dropped on each part of Thermanox coverslip divided into 4 parts, and dried in clean bench. Before this procedure, Thermanox coverslip was divided into 4 parts with scissors and laid overnight under the UV of a clean bench. After the transparent tape of the fertilized egg was removed with a knife and CAM was identified, sample-treated Thermanox was overturned with a pincette and sealed again with transparent tape. All used scissors, knifes, pincettes and so on were sterilized with 70% ethanol, and all pincette was sterilized whenever used for loading sample.

On day 7 (6.5-day embryo): The transparent tape was removed with a knife. 1 ml Intralipose (fat emulsion) was injected in right below of CAM with a syringe following removal of air bubble. Apparent blood vessel was observed on a white ground. Be careful to hurt the blood vessel when injecting Intralipose with a syringe. CAM were observed and then near photographed with a camera.

As a result, HSDVHK and HGDVHK showed different inhibitory effects on the angiogenesis in chick chorioallantoic membrane (CAM angiogenesis) in accord with the results of FIG. 9, whereas HHDVHK had little effect. The results were collectively shown in FIG. 10.

7-3) Growth Inhibition Assay of Subcutaneous Solid Tumor

Lewis lung carcinomas cells (1×10$^6$) were injected subcutaneously into dorsal midline of C57BL/6 mice. When tumors were 100-200 mm$^3$ in volume, the mice were randomized into three groups. Two groups received HGDVHK or HSDVHK (100 mg/kg mouse), respectively, in PBS via subcutaneous injection at a site distant from the tumor once daily. The other group (control group) received comparable injections of PBS alone. The sizes of the tumors in all groups were measured at the same time everyday. The experiments were terminated when the control mice began to die.

As a result, the growth of solid tumor made by injection of Lewis lung carcinomas cell was largely suppressed by the administration of 100 mg/kg mouse HSDVHK. This suppression is believed to be a result of anti-angiogenesis activity of HSDVHK. The results were collectively shown in FIGS. 11, 12 and 13.

On the basis of the above results, the integrin microarray of the present invention can be used to efficiently screen integrin-specific antagonistic peptide from peptide library, and peptides having unknown until now and unique amino acid sequences are developed from the results. At the same time, the biological activities of these antagonistic peptides were proved through in vitro human umverical vein endothelial cell migration test, in vivo angiogenesis assay of chick chorioallantoic membrane, and growth inhibition test of subcutaneous solid tumor.

INDUSTRIAL APPLICABILITY

As above, the present invention has the following effects.

Firstly, the present invention is applicable to screening of new drug candidate. High-throughput screening of integrin-specific antagonistic materials makes it possible to screen many candidates within short time because it is possible to rapidly screen a large amount of antagonistic proteins against labeled proteins related with some diseases.

Secondly, the integrin protein chip prepared by using ProteoChip™ is very sensitive because the detection limit of integrin-ligand reaction is really low. ELISA method, used until now for research of integrin-ligand interaction, has disadvantages like that it needs a large amount of protein and its reaction is non-specific. However, the method of the present invention using ProteoChip™ makes it possible to have a good result more sensitively and highly cost-effectively because the amount of protein needed in the present invention is 1,000 times less than the ELISA.

Thirdly, the present invention is used for research of protein-protein interaction. Even if the integrin-ligand interaction was studied with an example of integrin receptor, it is possible to investigate many other protein-protein interactions reacting to different proteins.

Fourthly, the applicability of the present invention is various. It can be used for interaction researches of protein-DNA, protein-small molecules (chemical compounds), protein-specific cells and so on.

Fifthly, the present invention provides new peptides having efficient integrin $\alpha_{IIb}\beta_3$- and integrin $\alpha_v\beta_3$-specific antagonistic activities, and these peptides can be used as anticancer drugs.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A high-throughput screening method of antagonistic material of integrin, comprising the steps of;
    (a) immobilizing integrin $\alpha_{IIb}\beta_3$ and/or $\alpha_v\beta_3$;
    (b) reacting ligand protein labeled with fluorescence and peptide pool of peptide library on the protein chip on which the integrin is immobilized;
    (c) washing the protein chip with buffer solution after the reacting; and
    (d) measuring the degree of ligand binding after the washing;
    said method providing a peptide having antagonistic activity of integrin $\alpha_v\beta_3$ that is selected from the group consisting of HSDVHK peptide (SEQ ID NO: 1), HGDVHK peptide (SEQ ID NO: 2), HHLLHK peptide (SEQ ID NO: 3), HGLVHK peptide (SEQ ID NO: 4), and HGDLHK peptide (SEQ ID NO: 5).

2. The high-throughput screening method of claim 1, wherein the ligand is any one selected from the group consisting of vitronectin, fibronectin, collagen, laminin, Von Willebrand Factor (vWF) and fibrinogen.

3. A pharmaceutical composition for treating cancer, comprising peptide of claim 1.

* * * * *